US011020725B2

(12) United States Patent
Kim et al.

(10) Patent No.: US 11,020,725 B2
(45) Date of Patent: Jun. 1, 2021

(54) METHOD OF PREPARING SUPERABSORBENT POLYMER

(71) Applicant: LG Chem, Ltd., Seoul (KR)

(72) Inventors: Jun Kyu Kim, Daejeon (KR); Hyung Ki Yoon, Daejeon (KR); Dae Woo Nam, Daejeon (KR); Bo Hyun Seong, Daejeon (KR); Yeon Woo Hong, Daejeon (KR); Seong Beom Heo, Daejeon (KR); Seon Jung Jung, Daejeon (KR); Ji Yoon Jeong, Daejeon (KR); Tae Hwan Jang, Daejeon (KR); Su Jin Kim, Daejeon (KR)

(73) Assignee: LG Chem, Ltd.

( * ) Notice: Subject to any disclaimer, the term of this patent is extended or adjusted under 35 U.S.C. 154(b) by 96 days.

(21) Appl. No.: 16/092,964

(22) PCT Filed: Jan. 5, 2017

(86) PCT No.: PCT/KR2017/000158
§ 371 (c)(1),
(2) Date: Oct. 11, 2018

(87) PCT Pub. No.: WO2018/117323
PCT Pub. Date: Jun. 28, 2018

(65) Prior Publication Data
US 2019/0134603 A1 May 9, 2019

(30) Foreign Application Priority Data

Dec. 20, 2016 (KR) ........................ 10-2016-0174933

(51) Int. Cl.
| | |
|---|---|
| *B01J 20/26* | (2006.01) |
| *B01J 20/30* | (2006.01) |
| *C08J 9/04* | (2006.01) |
| *C08J 3/12* | (2006.01) |
| *C08J 3/075* | (2006.01) |
| *C08F 2/44* | (2006.01) |
| *C08K 5/37* | (2006.01) |
| *C08J 3/24* | (2006.01) |
| *A61L 15/60* | (2006.01) |
| *B01J 20/28* | (2006.01) |
| *B01J 20/32* | (2006.01) |
| *C08F 20/06* | (2006.01) |

(52) U.S. Cl.
CPC ............. *B01J 20/267* (2013.01); *A61L 15/60* (2013.01); *B01J 20/28004* (2013.01); *B01J 20/28021* (2013.01); *B01J 20/3021* (2013.01); *B01J 20/3064* (2013.01); *B01J 20/3085* (2013.01); *B01J 20/321* (2013.01); *B01J 20/3219* (2013.01); *B01J 20/3282* (2013.01); *B01J 20/3293* (2013.01); *C08F 2/44* (2013.01); *C08F 20/06* (2013.01); *C08J 3/075* (2013.01); *C08J 3/12* (2013.01); *C08J 3/24* (2013.01); *C08J 3/245* (2013.01); *C08J 9/04* (2013.01); *C08K 5/37* (2013.01); *B01J 2220/68* (2013.01); *C08F 2810/20* (2013.01); *C08J 2333/02* (2013.01)

(58) Field of Classification Search
CPC ...................................................... B01J 20/267
See application file for complete search history.

(56) References Cited

U.S. PATENT DOCUMENTS

| | | | |
|---|---|---|---|
| 4,703,067 A | 10/1987 | Mikita et al. | |
| 5,338,766 A | 8/1994 | Phan et al. | |
| 10,065,175 B2 * | 9/2018 | Lee ......................... | C08F 20/10 |
| 10,759,912 B2 * | 9/2020 | Lee ........................ | C08K 11/00 |
| 2001/0038831 A1 | 11/2001 | Park et al. | |
| 2002/0120085 A1 * | 8/2002 | Matsumoto ............. | C08F 20/06 |
| | | | 526/317.1 |
| 2005/0137546 A1 | 6/2005 | Joy et al. | |
| 2010/0093949 A1 | 4/2010 | Herfert et al. | |
| 2010/0323885 A1 | 12/2010 | Herfert et al. | |
| 2012/0232176 A1 | 9/2012 | Lopez Villanueva et al. | |
| 2012/0258851 A1 * | 10/2012 | Nakatsuru ............. | C08F 220/06 |
| | | | 502/7 |
| 2013/0026412 A1 | 1/2013 | Machida et al. | |
| 2014/0312273 A1 * | 10/2014 | Wattebled ................ | C08J 3/245 |
| | | | 252/194 |
| 2015/0283284 A1 | 10/2015 | Azad et al. | |
| 2016/0108227 A1 | 4/2016 | Wattebled et al. | |
| 2016/0354757 A1 | 12/2016 | Lee et al. | |
| 2016/0375171 A1 | 12/2016 | Omori et al. | |
| 2017/0066862 A1 | 3/2017 | Matsumoto et al. | |
| 2018/0056274 A1 * | 3/2018 | Lee ........................ | B01J 20/267 |
| 2018/0178193 A1 | 6/2018 | Lee et al. | |

(Continued)

FOREIGN PATENT DOCUMENTS

| | | |
|---|---|---|
| CN | 103857714 A | 6/2014 |
| CN | 104212105 A | 12/2014 |

(Continued)

OTHER PUBLICATIONS

Extended European Search Report including the Written Opinion for Application No. EP 17885216.6 dated May 14, 2019.

(Continued)

*Primary Examiner* — Irina Krylova

(74) *Attorney, Agent, or Firm* — Lerner, David, Littenberg, Krumholz & Mentlik, LLP

(57) ABSTRACT

A superabsorbent polymer according to the present invention has excellent initial absorption properties, and thus it may be used in sanitary materials such as diapers, etc., thereby exhibiting excellent performances.

7 Claims, No Drawings

(56) References Cited

U.S. PATENT DOCUMENTS

| | | | |
|---|---|---|---|
| 2019/0135992 A1 | 5/2019 | Seong et al. | |
| 2019/0217272 A1* | 7/2019 | Hong | A61L 15/26 |
| 2019/0308170 A1* | 10/2019 | Heo | C08K 5/06 |

FOREIGN PATENT DOCUMENTS

| | | |
|---|---|---|
| CN | 104974312 A | 10/2015 |
| CN | 105980464 A | 9/2016 |
| CN | 109071831 A | 12/2018 |
| EP | 1589040 A1 | 10/2005 |
| EP | 2399944 A1 | 12/2011 |
| EP | 2518092 A1 | 10/2012 |
| EP | 2589613 A1 | 5/2013 |
| EP | 3248990 A1 | 11/2017 |
| EP | 3260485 A1 | 12/2017 |
| EP | 3318595 A1 | 5/2018 |
| EP | 3342802 A1 | 7/2018 |
| EP | 3424987 A1 | 1/2019 |
| JP | S63268748 A | 11/1988 |
| JP | H11302310 A | 11/1999 |
| JP | 2010510045 A | 4/2010 |
| JP | 2010520948 A | 6/2010 |
| JP | 2013511610 A | 4/2013 |
| KR | 20090121086 A | 11/2009 |
| KR | 20150116418 A | 10/2015 |
| KR | 20160010517 A | 1/2016 |
| KR | 20160063956 A | 6/2016 |
| KR | 20160102217 A | 8/2016 |
| KR | 20160128350 A | 11/2016 |
| KR | 20160141666 A | 12/2016 |
| WO | 2016195376 A1 | 12/2016 |

OTHER PUBLICATIONS

Third Party Observation for PCT/KR2017/000158 submitted Apr. 16, 2019.

Thomson Scientific, London, GB; AN 2016-76550Y; XP002791011; Dec. 8, 2016, 3 pages.

Odian, G..G., "Principles of Polymerization." Second Edition, John Wiley & Sons, Inc,, Copyright 1981, p. 203.

Schwalm, R., "UV Coatings; Basics, Recent Developments and New Applications." Elsevier Science, Dec. 21, 2006, p. 115.

International Search Report for PCT/KR2017/000158 dated Sep. 18, 2017.

Search Report in Chinese Office Action for Application No. 201780027800.4 dated Aug. 27, 2020; 3 pages.

Liutao Yang, et al, "Polymer Chemistry", Sichuan University Press, 2015, 4 pgs.

* cited by examiner

METHOD OF PREPARING SUPERABSORBENT POLYMER

CROSS-REFERENCE TO RELATED APPLICATION(S)

The present application is a national phase entry under 35 U.S.C. § 371 of International Application No. PCT/KR2017/000158, filed on Jan. 5, 2017, which claims priority to Korean Patent Application No. 10-2016-0174933, filed on Dec. 20, 2016, the disclosures of which are incorporated by reference herein.

TECHNICAL FIELD

The present invention relates to a method of preparing a superabsorbent polymer having excellent initial absorption properties.

BACKGROUND ART

A superabsorbent polymer (SAP) is a synthetic polymeric material capable of absorbing moisture from 500 to 1000 times its own weight. Various manufacturers have denominated it as different names, such as SAM (Super Absorbency Material), AGM (Absorbent Gel Material), etc. Since such superabsorbent polymers started to be practically applied in sanitary products, now they have been widely used not only for hygiene products such as disposable diapers for children, etc., but also for water retaining soil products for gardening, water stop materials for the civil engineering and construction, sheets for raising seedling, fresh-keeping agents for food distribution fields, materials for poultice or the like.

In most cases, these superabsorbent polymers are widely used in sanitary materials such as diapers, sanitary pads, etc. Inside the sanitary materials, the superabsorbent polymer is generally distributed throughout pulp. However, recent efforts have been continuously made to provide thinner sanitary materials such as diapers having a thinner thickness, etc., and as part of that, diapers having a reduced content of pulp, and furthermore, diapers having no pulp, so-called pulpless diapers are actively under development.

Such a sanitary material having a reduced content of pulp or having no pulp includes the superabsorbent polymer at a relatively high ratio, and the superabsorbent polymer particles are inevitably included as multiple layers in the sanitary materials. In order to allow the whole superabsorbent polymer particles included as multiple layers to more efficiently absorb liquid such as urine, it is necessary that the superabsorbent polymer basically exhibits high absorption performance and absorption rate. In particular, in order to improve dryness, which is a degree to which no liquid is left on the surface of the superabsorbent polymer after the liquid is absorbed by the superabsorbent polymer, excellent initial absorption properties are required.

To this end, superabsorbent polymers have been generally prepared by reverse-phase suspension polymerization or a foaming agent has been used in the preparation of superabsorbent polymers. However, the reverse-phase suspension polymerization requires an additional separate process, which is disadvantageous in the process, and requires use of a large amount of an organic solvent, and also has difficulty in recovering prepared superabsorbent polymers. Further, the method of using a foaming agent is to provide porosity by forming pores inside the superabsorbent polymer, but this method also has a limitation in that it is difficult to obtain uniform porous particles.

As such, there is a continuous demand for a superabsorbent polymer having excellent initial absorption properties in order to improve dryness.

DETAILED DESCRIPTION OF THE INVENTION

Technical Problem

The present invention provides a method of preparing a superabsorbent polymer having excellent initial absorption properties.

Further, the present invention provides a superabsorbent polymer prepared by the above preparation method.

Technical Solution

In order to achieve the above objects, the present invention provides a method of preparing a superabsorbent polymer, the method comprising the following steps of:

performing crosslinking polymerization of a water-soluble ethylene-based unsaturated monomer having acidic groups which are at least partially neutralized in the presence of an internal crosslinking agent and a surfactant to form a hydrogel polymer containing a first crosslinked polymer (Step 1);

drying, pulverizing, and size-sorting the hydrogel polymer to form a base polymer powder (Step 2); and performing surface-crosslinking of the base polymer powder by heat treatment in the presence of a surface crosslinking solution to form superabsorbent polymer particles (Step 3), wherein a maximum foaming point reaches within 100 seconds from a polymerization initiation point of the water-soluble ethylene-based unsaturated monomers in Step 1.

In order to improve initial absorption properties of the superabsorbent polymer, pores are introduced into the inside of the superabsorbent polymer, and to this end, a foaming agent is known to be used during polymerization of the superabsorbent polymer. Pores may be introduced by using the foaming agent, but there is a problem that generated bubbles are not uniformly distributed throughout the superabsorbent polymer. In order to improve this problem, a surfactant is used. However, although the surfactant is used, there is a limitation in uniform distribution of pores which are homogeneous in size. Therefore, there is a limitation in improving initial absorption properties of the superabsorbent polymer.

Accordingly, the present invention confirmed that initial absorption properties of superabsorbent polymers may be improved by using a foaming agent and a surfactant while adjusting a time taken for the foaming agent to foam bubbles and to reach a maximum foaming point, as described below. It was confirmed that the time taken to reach the maximum foaming point influences the initial absorption properties of superabsorbent polymers, as described in the following Examples and Comparative Examples.

Hereinafter, each step of the present invention will be described in detail.

(Step 1)

Step 1 is a step of forming the hydrogel polymer by performing crosslinking polymerization of a monomer composition including the internal crosslinking agent, the foaming agent, and the water-soluble ethylene-based unsaturated monomers having acidic groups which are at least partially neutralized.

The water-soluble ethylene-based unsaturated monomer constituting the first crosslinked polymer may be any monomer commonly used in the preparation of superabsorbent polymers. Non-limiting examples of the water-soluble ethylene-based unsaturated monomer may be a compound represented by the following Chemical Formula 1:

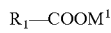  [Chemical Formula 1]

in Chemical Formula 1, $R_1$ is an alkyl group containing an unsaturated bond and having 2 to 5 carbon atoms, and $M^1$ is a hydrogen atom, a monovalent or divalent metal, an ammonium group, or an organic amine salt.

Preferably, the monomer may include one or more selected from the group consisting of acrylic acid, methacrylic acid, and a monovalent metal salt thereof, a divalent metal salt thereof, an ammonium salt thereof, and an organic amine salt thereof. When acrylic acid or a salt thereof is used as the water-soluble ethylene-based unsaturated monomer, it is advantageous in that a superabsorbent polymer having improved absorbency may be obtained. In addition, as the monomer, maleic anhydride, fumaric acid, crotonic acid, itaconic acid, 2-acryloylethane sulfonic acid, 2-methacryloylethane sulfonic acid, 2-(meth)acryloylpropane sulfonic acid, 2-(meth)acrylamide-2-methyl propane sulfonic acid, (meth)acrylamide, N-substituted (meth)acrylate, 2-hydroxyethyl(meth)acrylate, 2-hydroxypropyl(meth)acrylate, methoxy polyethylene glycol (meth)acrylate, polyethylene glycol (meth)acrylate, (N,N)-dimethylaminoethyl(meth)acrylate, or (N,N)-dimethylaminopropyl(meth)acrylamide may be used.

Here, the water-soluble ethylene-based unsaturated monomer may have acidic groups which are at least partially neutralized. Preferably, those partially neutralized with an alkali substance such as sodium hydroxide, potassium hydroxide, ammonium hydroxide, etc. may be used.

In this regard, a degree of neutralization of the monomer may be 40 mole % to 95 mole %, or 40 mole % to 80 mole %, or 45 mole % to 75 mole %. The range of the neutralization degree may vary depending on final physical properties. An excessively high degree of neutralization renders the neutralized monomers precipitated, and thus polymerization may not occur readily, whereas an excessively low degree of neutralization not only greatly deteriorates absorbency of the polymer but also endows the polymer with hard-to-handle properties, such as of elastic rubber.

Further, a concentration of the water-soluble ethylene-based unsaturated monomer in the monomer composition may be properly controlled, in consideration of a polymerization time and reaction conditions, and the concentration may be preferably 20% by weight to 90% by weight, or 40% by weight to 65% by weight, which is for using the gel effect during the polymerization reaction in a high-concentration aqueous solution to eliminate a need for removing unreacted monomers after the polymerization and also for improving pulverization efficiency upon a subsequent pulverization process of the polymer. However, if the concentration of the monomer is too low, a yield of the superabsorbent polymer may become low. On the contrary, if the concentration of the monomer is too high, there is a process problem that a part of the monomers is precipitated, or pulverization efficiency is lowered upon pulverization of the polymerized hydrogel polymer, and physical properties of the superabsorbent polymer may be deteriorated.

Further, the surfactant functions to uniformly distribute bubbles throughout the polymer while maintaining the shape of the bubbles formed during polymerization, and functions to increase the surface area of the polymer. Preferably, the surfactant may be a cationic surfactant, an anionic surfactant, or a non-ionic surfactant.

For example, the anionic surfactant may be a compound represented by the following Chemical Formula 2, and more preferably, sodium dodecyl sulfate.

  [Chemical Formula 2]

in Chemical Formula 2,

R is an alkyl group having 8 to 16 carbon atoms.

Further, the non-ionic surfactant may be exemplified by sugar ester. As the sugar ester, sucrose stearate or sucrose isobutylate may be used.

Further, the surfactant may be preferably used in an amount of 0.3% by weight or less with respect to the weight of the water-soluble ethylene-based unsaturated monomer. If the amount of the surfactant is more than 0.3% by weight, there is no substantial improvement effect, and the content of the surfactant in the superabsorbent polymer is increased, which is not preferable. Further, the surfactant may be preferably used in an amount of 0.001% by weight or more with respect to the weight of the water-soluble ethylene-based unsaturated monomer.

Further, the monomer composition may include a foaming agent as needed. The foaming agent foams bubbles during polymerization to form pores in the hydrogel polymer, thereby increasing the surface area. The foaming agent may be an inorganic foaming agent or an organic foaming agent. Examples of the inorganic foaming agent may include sodium bicarbonate, sodium carbonate, potassium bicarbonate, potassium carbonate, calcium bicarbonate, calcium carbonate, magnesium bicarbonate, and magnesium carbonate. Further, examples of the organic foaming agent may include 2,2'-azobis(2-methylpropionamidine) dihydrochloride (AAPH), azodicarbonamide (ADCA), dinitroso pentamethylene tetramine (DPT), p,p'-oxybisbenzenesulfonylhydrazide (OBSH), and p-toluenesulfonyl hydrazide (TSH).

Further, the foaming agent may be preferably used in an amount of 1.0% by weight or less with respect to the weight of the water-soluble ethylene-based unsaturated monomer. If the amount of the foaming agent is more than 1.0% by weight, too many pores are formed to deteriorate gel strength of the superabsorbent polymer and to decrease density, which may cause problems in distribution and storage. Further, the foaming agent may be preferably used in an amount of 0.01% by weight or more with respect to the weight of the water-soluble ethylene-based unsaturated monomer.

Further, as the internal crosslinking agent, any compound is possible as long as it enables introduction of crosslinkage upon polymerization of the water-soluble ethylene-based unsaturated monomers. Non-limiting examples of the internal crosslinking agent may include multifunctional crosslinking agents, such as N,N'-methylenebisacrylamide, trimethylolpropane tri(meth)acrylate, ethylene glycol di(meth)acrylate, polyethylene glycol(meth)acrylate, propylene glycol di(meth)acrylate, polypropylene glycol(meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaerythritol pentacrylate, glycerin tri(meth)acrylate, pentaerythritol tetraacrylate, triarylamine, ethylene glycol diglycidyl ether, propylene glycol, glycerin, or ethylene carbonate, which may be used alone or in combination of two or more thereof, but are not limited thereto. Preferably, two kinds of polyethylene glycol diacrylates having different molecular weights may be used.

The internal crosslinking agent may be added at a concentration of about 0.001% by weight to 1% by weight with respect to the monomer composition. That is, if the concentration of the internal crosslinking agent is too low, the polymer may have a low absorption rate and low gel strength, undesirably. On the contrary, if the concentration of the internal crosslinking agent is too high, the polymer may have a low absorption ability, which is not preferred as an absorbent.

In step 1, a thermal polymerization initiator, a photopolymerization initiator, or a redox initiator which is generally used in the preparation of superabsorbent polymers may be included.

One or more compounds selected from the group consisting of persulfate-based initiators, azo-based initiators, hydrogen peroxide, and ascorbic acid may be used as the thermal polymerization initiator. Specific examples of the persulfate-based initiators may include sodium persulfate ($Na_2S_2O_8$), potassium persulfate ($K_2S_2O_8$), ammonium persulfate (($NH_4$)$_2S_2O_8$) or the like. Examples of the azo-based initiators may include 2,2-azobis(2-amidinopropane)dihydrochloride, 2,2-azobis-(N,N-dimethylene)isobutyramidine dihydrochloride, 2-(carbamoylazo)isobutylonitril, 2,2-azobis(2-[2-imidazolin-2-yl]propane)dihydrochloride, 4,4-azobis-(4-cyanovaleric acid) or the like. More various thermal polymerization initiators are disclosed in "Principle of Polymerization (Wiley, 1981)" written by Odian, p. 203, which may be served as a reference.

As the photo-polymerization initiator, for example, one or more compounds selected from the group consisting of benzoin ether, dialkyl acetophenone, hydroxyl alkylketone, phenyl glyoxylate, benzyl dimethyl ketal, acyl phosphine, and α-aminoketone may be used. Among them, specific example of acyl phosphine may include commercial lucirin TPO, namely, 2,4,6-trimethyl-benzoyl-trimethyl phosphine oxide. More various photo-polymerization initiators are disclosed in "UV Coatings: Basics, Recent Developments and New Application (Elsevier, 2007)" written by Reinhold Schwalm, p. 115, which may be served as a reference.

Further, a reducing agent that facilitates decomposition of the above-described polymerization initiators may be used in combination, and a combination thereof may be used as a redox initiator. As the reducing agent, a sulfite such as sodium sulfite, sodium bisulfite, etc., a reducing metal such as a ferrous salt, etc., L-ascorbic acid, or amines may be used alone or in combination of two or more thereof, but is not limited thereto.

The polymerization initiator may be added at a concentration of about 0.001% by weight to about 1% by weight with respect to the monomer composition. That is, if the concentration of the polymerization initiator is too low, the polymerization rate becomes low and thus a large amount of residual monomers may be undesirably extracted from the final product. On the contrary, if the concentration of the polymerization initiator is higher than the above range, polymer chains constituting a network become short, and thus the content of water-soluble components is increased and physical properties of the polymer may deteriorate, such as a reduction in absorbency under load.

In addition, the monomer composition may further include additives such as a thickener, a plasticizer, a preservation stabilizer, an antioxidant, etc., as needed.

Further, the monomer composition may be prepared in a solution form, in which the raw materials such as the above-described monomers, etc. are dissolved in a solvent.

In this regard, as the usable solvent, any solvent may be used without limitations in the constitution, as long as it is able to dissolve the above-described raw materials. For example, water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, N,N-dimethylacetamide, or a mixture thereof may be used as the solvent.

In this regard, thermal polymerization or UV polymerization of the monomer composition may be performed by a common method without particular limitation in the conditions. Specifically, thermal polymerization may be divided into a redox polymerization which is performed at a temperature of 30° C. to 100° C. for 2 minutes to 30 minutes and a thermal polymerization performed for 2 minutes to 30 minutes. Further, UV polymerization (photo-polymerization) may be performed by irradiating lights at a temperature of 30° C. to 90° C. for 10 seconds to 5 minutes. Further, upon UV irradiation, UV intensity may be 0.1 mW/cm$^2$ to 30 mW/cm$^2$. A light source and wavelength range for UV irradiation are also well known to those skilled in the art.

For example, the monomer composition is injected to a reactor like a kneader equipped with the agitating spindles, and thermal polymerization is performed by providing hot air thereto or by heating the reactor so as to obtain the hydrogel polymer. In this regard, the hydrogel polymer may have a size of centimeters or millimeters when it is discharged from an outlet of the reactor, according to the type of agitating spindles equipped in the reactor. Specifically, the hydrogel polymer may be obtained in various forms according to a concentration of the monomer composition fed thereto, a feeding speed or the like, and the hydrogel polymer having a (weight average) particle size of 2 mm to 50 mm may be generally obtained.

For another example, formation of the hydrogel polymer may be performed by common UV initiation. In this case, the reaction may be performed by injecting the monomer composition into a chamber containing a UV irradiation device and a tray, and then irradiating UV thereto. When the obtained hydrogel polymer is pulverized by a meat chopper, particles having a size of millimeters or centimeters may be generally obtained.

In this regard, polymerization of the monomer composition is preferably performed at a temperature of 30° C. to 80° C. Within this temperature range, a time taken from the polymerization initiation point of the water-soluble ethylene-based unsaturated monomer to the maximum foaming point may be easily controlled below 100 seconds.

The 'polymerization initiation point' refers to a point at which the polymerization of the monomer composition is initiated, for example, a point at which heat is applied in the case of thermal polymerization, a point at which light irradiation is initiated in the case of photo-polymerization, and a point at which oxidation-reduction catalysts come into contact with each other in the case of oxidation-reduction polymerization. Further, the 'maximum foaming point' refers to a point at which foaming occurs by the foaming agent in the monomer composition, and thus a volume of the monomer composition is maximized.

Preferably, the time taken from the polymerization initiation point of the water-soluble ethylene-based unsaturated monomer to the maximum foaming point may be 90 seconds or less or 85 seconds or less. Further, the time taken from the polymerization initiation point of the water-soluble ethylene-based unsaturated monomer to the maximum foaming point may be 5 seconds or more, 6 seconds or more, 7 seconds or more, 8 seconds or more, 9 seconds or more, or 10 seconds or more.

Meanwhile, the hydrogel polymer obtained by the above method may have a water content of 40% by weight to 80% by weight. The "water content", as used herein, means a water weight in the total weight of the hydrogel polymer, which is obtained by subtracting the weight of the dry polymer from the weight of the hydrogel polymer. Specifically, the water content is defined as a value calculated by measuring a weight loss according to evaporation of water in the polymer during a drying process of increasing the temperature of the polymer with infrared heating. In this regard, the drying conditions may be determined as follows; the temperature may be increased from room temperature to about 180° C. and then the temperature may be maintained at 180° C., and the total drying time may be determined as 20 minutes, including 5 minutes for the temperature rising step.

(Step 2)

Step 2 is a step of drying, pulverizing, and size-sorting the hydrogel polymer prepared in Step 1 to form a base polymer powder. The base polymer powder and the superabsorbent polymer obtained therefrom may be appropriately prepared and provided so that they are allowed to have a particle size of 150 μm to 850 μm. More specifically, at least 95% by weight or more of the base polymer powder and the superabsorbent polymer obtained therefrom may have a particle size of 150 μm to 850 μm, and the amount of fine powder having a particle size of less than 150 μm may be less than 3% by weight. By controlling the particle size distribution of the base polymer powder and the superabsorbent polymer within the preferred range, the superabsorbent polymer finally prepared may exhibit better physical properties described above.

Meanwhile, drying, pulverizing, and size-sorting methods will be described in more detail as follows.

First, in drying the hydrogel polymer, a coarse pulverization step may be further carried out before drying, in order to increase efficiency of the drying step, if necessary. In this regard, there is no limitation in the constitution of a milling machine to be used. Specifically, any one device selected from the group consisting of a vertical pulverizer, a turbo cutter, a turbo grinder, a rotary cutter mill, a cutter mill, a disc mill, a shred crusher, a crusher, a chopper, and a disc cutter may be used, but it is not limited thereto.

In this regard, the coarse pulverization step may be performed so that the hydrogel polymer is allowed to have a particle size of about 2 mm to about 10 mm. Due to the high water content, it is technically not easy to pulverize the hydrogel polymer to a particle size of less than 2 mm, and the pulverized particles may agglomerate together. Meanwhile, when the particle size is larger than 10 mm, the effect of increasing efficiency of the subsequent drying step may be unsatisfactory.

The hydrogel polymer coarsely pulverized or the hydrogel polymer not coarsely pulverized immediately after the polymerization is subjected to drying. In this regard, a drying temperature of the drying step may be 50° C. to 250° C. When the drying temperature is lower than 50° C., there is a concern about excessively long drying time or deterioration of the physical properties of the superabsorbent polymer finally formed, and when the drying temperature is higher than 250° C., only the surface of the polymer is dried, and thus there is a concern about generation of fine powder during the subsequent pulverization process and deterioration of the physical properties of the superabsorbent polymer finally formed. More preferably, the drying may be performed at a temperature of 150° C. to 200° C., and more preferably at a temperature of 160° C. to 190° C. Meanwhile, the drying time may be 20 minutes to about 15 hours, considering the process efficiency, but is not limited thereto.

Furthermore, any drying process may be selected and used without limitation in the constitution, as long as it may be commonly used. Specifically, the drying step may be carried out by a method of supplying hot air, irradiating infrared rays, irradiating microwaves, irradiating ultraviolet rays, etc. When the drying step as above is finished, the water content of the polymer may be 0.05% by weight to 10% by weight.

Next, the dried polymer obtained from the drying step is subjected to a pulverization step.

In the polymer powder obtained after the pulverization step, a content of powder having a particle size of 150 μm to 850 μm may be preferably 90% or more. Specific example of a milling machine used to pulverize the polymer into the above particle size may include a ball mill, a pin mill, a hammer mill, a screw mill, a roll mill, a disc mill, a jog mill, etc., but the present disclosure is not limited to the above-described examples.

To manage the physical properties of the superabsorbent polymer powder to be finally manufactured after the pulverization step, the polymer powder obtained after pulverization may be subjected to an additional process of sorting the polymer powder according to the particle size. Preferably, polymers having a particle size of 150 μm to 850 μm are sorted. Only a polymer powder having this particle size may be applied to a surface crosslinking reaction step described below, and finally commercialized. In the polymer powder, the content of the polymer powder having a particle size of 150 μm to 850 μm is more preferably 90% or more.

Further, the prepared base polymer powder may preferably have centrifuge retention capacity (CRC) of 25 g/g to 60 g/g, and an absorption rate (vortex) of 20 seconds to 50 seconds.

(Step 3)

Step 3 is a step of performing surface-crosslinking of the base polymer prepared in Step 2, wherein surface-crosslinking of the base polymer powder is carried out by heat treatment in the presence of a surface crosslinking solution containing a surface crosslinking agent to form superabsorbent polymer particles.

Here, a kind of the surface crosslinking agent contained in the surface crosslinking solution is not particularly limited. Non-limiting examples of the surface-crosslinking agent may include one or more compounds selected from the group consisting of ethylene glycol diglycidyl ether, polyethylene glycol diglycidyl ether, glycerol polyglycidyl ether, propylene glycol diglycidyl ether, polypropylene glycol diglycidyl ether, ethylene glycol, diethylene glycol, propylene glycol, triethylene glycol, tetraethylene glycol, propanediol, dipropylene glycol, polypropylene glycol, glycerin, polyglycerin, butanediol, heptanediol, hexanediol, trimethylol propane, pentaerythritol, sorbitol, calcium hydroxide, magnesium hydroxide, aluminum hydroxide, iron hydroxide, calcium chloride, magnesium chloride, aluminum chloride, and iron chloride.

In this regard, a content of the surface crosslinking agent may be preferably 0.01 part by weight to 5 parts by weight with respect to 100 parts by weight of the base polymer. If the content of the surface crosslinking agent exceeds 5 parts by weight, excessive surface crosslinking may occur. Thus, when the superabsorbent polymer absorbs water, a large amount of water is present on the surface, and thus there is a problem that dryness is lowered.

Further, the surface crosslinking solution may further include one or more solvents selected from the group consisting of water, ethanol, ethylene glycol, diethylene glycol, triethylene glycol, 1,4-butanediol, propylene glycol, ethylene glycol monobutylether, propylene glycol monomethylether, propylene glycol monomethylether acetate, methylethylketone, acetone, methylamylketone, cyclohexanone, cyclopentanone, diethylene glycol monomethylether, diethyleneglycol ethylether, toluene, xylene, butylolactone, carbitol, methylcellosolve acetate, and N,N-dimethyl acetamide, and preferably, water. The solvent may be used in an amount of 0.5 parts by weight to 10 parts by weight with respect to 100 parts by weight of the base polymer powder.

Further, the surface crosslinking solution may include an inorganic filler. The inorganic filler may include silica, aluminum oxide, or silicate. The inorganic filler may be included in an amount of 0.01 parts by weight to 0.5 parts by weight with respect to 100 parts by weight of the base polymer powder.

Further, the surface crosslinking solution may further include a thickener. When surface-crosslinking of the base polymer powder is further performed in the presence of the thickener, reduction of physical properties may be minimized even after pulverization. Specifically, the thickener may be one or more selected from polysaccharides and hydroxyl-containing polymers. The polysaccharides may include gum-based thickeners and cellulose-based thickeners. Specific examples of the gum-based thickeners may include xanthan gum, arabic gum, karaya gum, tragacanth gum, ghatti gum, guar gum, locust bean gum, and *psyllium* seed gum, etc., and specific examples of the cellulose-based thickeners may include hydroxypropylmethylcellulose, carboxymethylcellulose, methylcellulose, hydroxymethylcellulose, hydroxyethylcellulose, hydroxypropylcellulose, hydroxyethylmethylcellulose, hydroxymethylpropylcellulose, hydroxyethylhydroxypropylcellulose, ethylhydroxyethylcellulose, methylhydroxypropylcellulose, etc. Meanwhile, specific examples of the hydroxyl-containing polymers may include polyethylene glycol, polyvinyl alcohol, etc.

Meanwhile, to perform the surface crosslinking, a method of feeding the surface crosslinking solution and the base polymer to a reactor and mixing them, a method of spraying the surface crosslinking solution onto the base polymer, or a method of mixing the base polymer and the surface crosslinking solution while continuously feeding them to a mixer being continuously operated may be used.

The surface modification step may be performed at a temperature of 100° C. to 250° C. Further, the surface modification may be performed for 1 minute to 120 minutes, preferably 1 minute to 100 minutes, and more preferably 10 minutes to 60 minutes. That is, to induce a minimal surface crosslinking reaction and to prevent deterioration of the physical properties by damage of the polymer particles due to excessive reaction, the surface modification step may be performed under the above-described conditions.

Superabsorbent Polymer

The superabsorbent polymer prepared by the above-described preparation method of the present invention has excellent initial absorption properties.

Specifically, the superabsorbent polymer according to the present invention has an absorption rate of 45 seconds or less, as measured according to a vortex measurement method. The absorption rate means a time taken for a vortex to disappear by rapid absorption when the superabsorbent polymer in physiological saline is stirred, and it may define a high absorption rate of the superabsorbent polymer. Preferably, the absorption rate, as measured according to the vortex measurement method, may be 40 seconds or less, 39 seconds or less, 38 seconds or less, 37 seconds or less, 36 seconds or less, or 35 seconds or less. Further, as this value is lower, the absorption rate is more excellent. A lower limit of the absorption rate is theoretically 0 second, but, for example, 10 second or more, or 20 seconds or more. Further, the vortex measurement method will be further specified in the following Examples.

Further, the superabsorbent polymer according to the present invention has 1 min-absorbency of 30 g/g or more for a 0.9 wt % sodium chloride aqueous solution. A method of measuring the absorbency will be further specified in the following Examples. Preferably, 1 min-absorbency for 0.9 wt % sodium chloride aqueous solution is 31 g/g or more, or 32.0 g/g or more. Further, as this value is higher, the absorbency is more excellent. A substantial upper limit of the absorbency is not limited, but, for example, 60 g/g or less, or 55 g/g or less.

Further, the superabsorbent polymer according to the present invention has 1 min-absorbency of 100 g/g or more for distilled water. A method of measuring the absorbency will be further specified in the following Examples. Preferably, 1 min-absorbency for distilled water is 110 g/g or more, or 120.0 g/g or more. Further, as this value is higher, the absorbency is more excellent. A substantial upper limit of the absorbency is not limited, but, for example, 250 g/g or less, or 240 g/g or less.

Further, the superabsorbent polymer according to the present invention has 30 min-centrifuge retention capacity (CRC) of 25 g/g or more for a 0.9 wt % sodium chloride aqueous solution. A method of measuring the centrifuge retention capacity will be further specified in the following Examples. Preferably, the centrifuge retention capacity is 26 g/g or more, or 27 g/g or more. Further, as this value is higher, the centrifuge retention capacity is more excellent. A substantial upper limit of the centrifuge retention capacity is not limited, but, for example, 45 g/g or less, or 40 g/g or less.

Further, the superabsorbent polymer according to the present invention has 1 hr-absorbency under 0.3 psi pressure (0.3 AUP) of 25 g/g or more. A method of measuring the absorbency under pressure will be further specified in the following Examples. Preferably, 0.3 AUP is 26 g/g or more, or 27 g/g or more. Further, as this value is higher, the absorbency under pressure is more excellent. A substantial upper limit of the absorbency under pressure is not limited, but, for example, 45 g/g or less, or 40 g/g or less.

Further, a percentage of particles having a particle size of 150 μm to 850 μm in the superabsorbent polymer according to the present invention is 90% or more.

Advantageous Effects

As described above, a superabsorbent polymer according to the present invention has excellent initial absorption properties, and thus it may be used in sanitary materials such as diapers, etc., thereby exhibiting excellent performances.

DETAILED DESCRIPTION OF THE EMBODIMENTS

Hereinafter, the preferred Examples are provided for better understanding. However, the following Examples are for illustrative purposes only, and the present invention is not intended to be limited by these Examples.

Example 1

In a 2 L-glass reactor surrounded by a jacket through which a heating medium pre-cooled at 25° C. was circulated, 500 g of acrylic acid, 0.05 g of IRGACURE 819, and 0.05 g of sodium dodecyl sulfate (SDS) were mixed with each other. 2.5 g of polyethylene glycol diacrylate (PEGDA, Mw=400) was injected thereto. 800 g of a 24% caustic soda solution was slowly added dropwise thereto, followed by mixing. A degree of neutralization of acrylic acid in sodium acrylate as a water-soluble ethylene-based unsaturated monomer thus obtained was 70 mole %.

After confirming that a temperature of the mixture increased to 72° C. or higher by neutralization heat generated upon mixing the two solutions, the mixture was left until the reaction temperature reached 40° C. When the reaction temperature reached 40° C., 0.5 g of sodium bicarbonate (SBC) in a solid phase was mixed with monomers, and 54 g of a 2% sodium persulfate solution diluted with water was injected at the same time.

The solution was poured in a tray (15 cm in width×15 cm) installed in a square polymerizer which had a UV irradiation device installed at the top thereof and had been preheated to 80° C., and polymerization was initiated by UV irradiation. 30 seconds later, gel was generated from the surface, and at a time point of 60 seconds after bubble formation was initiated, bubble formation reached a maximum point. After the bubble formation reached the maximum point, the reaction was allowed for additional 3 minutes, and a sheet-type polymer was cut in a size of about 5 cm×5 cm and then introduced into a meat chopper to pulverize the polymer. Finally, water-containing particles having a size of 1 mm to 10 mm were obtained.

The water-containing particles were dried in a hot air oven. Specifically, the water-containing particles were uniformly dried by flowing hot air at 180° C. from the bottom to the top for 15 minutes and from the top to the bottom for 15 minutes. After drying, the dried product had a water content of 2% or less.

After drying, the product was pulverized using a food mixer and sorted by a standard test sieve, and particles having a size of 150 μm to 850 μm were selected to prepare a base polymer.

Thereafter, 100 g of the prepared base polymer was mixed with a mixture containing 3 g of water, 3 g of methanol, 0.2 g of ethylene glycol diglycidyl ether, and 0.05 g of aerosol 200 by using a high speed mixer, and reaction was allowed at 140° C. for 40 minutes. The mixture was cooled to room temperature, and then a superabsorbent polymer having a particle size of 150 μm to 850 μm was obtained by using a standard test sieve.

Examples 2 to 4

A superabsorbent polymer was prepared in the same manner as in Example 1, except that in Example 1, the UV initiator (IRGACURE 819) and the surfactant stabilizer (SDS) were used in amounts as in the following Table 1.

Example 5

In Example 1, when the temperature of the mixture reached 60° C., sodium bicarbonate and the sodium persulfate solution were injected, and polymerization was initiated in a polymerizer which had been preheated to 80° C. 25 seconds after light irradiation, gel was generated from the surface, and at a time point of 40 seconds after bubble formation was initiated, bubble formation reached a maximum point. Thereafter, in the same manner as in Example 1, a superabsorbent polymer was prepared.

Comparative Example 1

In Example 1, when the temperature of the mixture reached 20° C., sodium bicarbonate and the sodium persulfate solution were injected, and polymerization was initiated in a polymerizer which had been preheated to 80° C. 35 seconds after light irradiation, gel was generated from the surface, and at a time point of 105 seconds after bubble formation was initiated, bubble formation reached a maximum point. Thereafter, in the same manner as in Example 1, a superabsorbent polymer was prepared.

Comparative Example 2

In Example 1, 0.015 g of IRGACUR 819 was used, and when the temperature of the mixture reached 20° C., sodium bicarbonate and the sodium persulfate solution were injected, and polymerization was initiated in a polymerizer which had been preheated to 80° C. 65 seconds after light irradiation, gel was generated from the surface, and at a time point of 158 seconds after bubble formation was initiated, bubble formation reached a maximum point. Thereafter, in the same manner as in Example 1, a superabsorbent polymer was prepared.

Experimental Example: Evaluation of Physical Properties of Superabsorbent Polymers Physical properties of the superabsorbent polymers prepared in Examples and Comparative Examples were evaluated by the following methods.

(1) Centrifuge Retention Capacity (CRC)

Centrifuge retention capacity (CRC) by absorbency under no load was measured for the respective superabsorbent polymers of Examples and Comparative Examples in accordance with European Disposables and Nonwovens Association (EDANA) standard WSP 241.3.

In detail, each polymer $W_0$ (g, about 0.2 g) of Examples and Comparative Examples was uniformly placed into a nonwoven-fabric-made bag, followed by sealing. Then, the bag was immersed at room temperature in a physiological saline solution which is a sodium chloride aqueous solution of 0.9% by weight. After 30 minutes, the bag was drained at 250 G for 3 minutes with a centrifuge, and the weight $W_2$ (g) of the bag was then measured. Further, the same procedures were carried out without the superabsorbent polymer, and the resultant weight $W_1$ (g) was measured.

Thus, CRC (g/g) was calculated from the obtained weights according to the following Equation 1:

$$\text{CRC}(g/g) = \{[W_2(g) - W_1(g) - W_0(g)]/W_0(g)\} \quad \text{[Equation 1]}$$

in Equation 1, $W_0$ (g) is an initial weight (g) of the superabsorbent polymer, $W_1$ (g) is a weight (g) of an apparatus without the superabsorbent polymer, which is measured after immersing in a physiological saline solution for 30 minutes and draining water off at 250 G for 3 minutes using a centrifuge, and $W_2$ (g) is the weight (g) of the apparatus including the superabsorbent polymer, which is measured after immersing the superabsorbent polymer in the physiological saline solution at room temperature for 30 minutes and draining water off at 250 G for 3 minutes using a centrifuge.

CRC (BR CRC) was also measured for the respective base polymers prepared in Examples and Comparative Examples in the same manner as above.

(2) Absorption Rate (Vortex)

50 mL of a 0.9 wt % NaCl solution and a magnetic bar with a size of 30 mm were placed in a 100 ml beaker. Under stirring at 600 rpm by a magnetic stirrer, 2.0 g of each of the superabsorbent polymers prepared in Examples and Comparative Examples was fed thereto when the NaCl solution reached 24° C. A time taken for a liquid vortex produced by stirring to disappear and for the liquid surface to be completely level was measured. This result was expressed as a vortex removal time (absorption rate; vortex).

Further, from the respective base polymers prepared in the preparation processes of Examples and Comparative Examples, particles of 300 μm to 600 μm were taken, and absorption rates (BR Vortex) thereof were measured in the same manner as above.

(3) 1 Min-Absorbency (0.9 wt % NaCl)

1 g of each of the superabsorbent polymers of Examples and Comparative Examples was placed in a 250 mL beaker, and immersed in 150 mL of 0.9 wt % sodium chloride aqueous solution at 24° C. for 1 minute. A 100-mesh standard sieve having a diameter of 90 mm was placed on the top of another 250 mL beaker, and all the immersed superabsorbent polymer was poured on the standard sieve, and then drained for 1 minute. The amount of the gel remaining on the standard sieve was measured, and regarded as 1 min-absorbency.

(4) 1 Min-Absorbency (Distilled Water)

1.0 g ($W_3$) of each of the superabsorbent polymers of Examples and Comparative Examples was placed into a nonwoven-fabric-made bag (15 cm×15 cm), which was immersed in 500 mL of distilled water at 24° C. for 1 minute. 1 minute later, the bag was taken from distilled water, and hung for 1 minute. Thereafter, the weight ($W_5$) of the bag was measured. Further, the same procedures were performed without the superabsorbent polymers, and the weight ($W_4$) was measured.

1 min-absorbency was calculated from the obtained weights according to the following Equation 2:

$$\text{1 min-absorbency(distilled water)} = \{[W_5(g) - W_4(g) - W_3(g)]/W_3(g)\} \quad \text{[Equation 2]}$$

in Equation 2, $W_3$ (g) is an initial weight (g) of the superabsorbent polymer, $W_4$ (g) is a weight (g) of an apparatus without the superabsorbent polymer, which is measured after immersing in distilled water for 1 minute, and $W_5$ (g) is the weight (g) of the apparatus including the superabsorbent polymer, which is measured after immersing in distilled water for 1 minute.

(5) Absorbency Under Pressure (AUP)

Absorbency under pressure (AUP) was measured for the respective superabsorbent polymers of Examples and Comparative Examples in accordance with European Disposables and Nonwovens Association EDANA standard WSP 242.3.

In detail, a 400 mesh stainless steel net was installed in the bottom of a plastic cylinder having an internal diameter of 60 mm. Each $W_0$ (g, 0.90 g) of the superabsorbent polymers obtained in Examples and Comparative Examples was uniformly scattered on the stainless steel net under conditions of a temperature of 23±2° C. and relative humidity of 45%. A piston which may uniformly provide a load of 0.3 psi was put thereon, in which an external diameter of the piston was slightly smaller than 60 mm, there was no gab between the internal wall of the cylinder and the piston, and the jig-jog of the cylinder was not interrupted. At this time, the weight $W_6$ (g) of the apparatus was measured.

After putting a glass filter having a diameter of 125 mm and a thickness of 5 mm in a petri dish having a diameter of 150 mm, a physiological saline solution composed of 0.9% by weight of sodium chloride was poured until the surface level of the physiological saline solution became equal to the upper surface of the glass filter. A sheet of filter paper having a diameter of 120 mm was put on the glass filter. The measurement apparatus was mounted on the filter paper, thereby getting the liquid absorbed under the load for 1 hour. 1 hour later, the weight $W_7$ (g) was measured after lifting the measurement apparatus up.

AUP (g/g) was calculated from the obtained weights according to the following Equation 3:

$$\text{AUP}(g/g) = [W_7(g) - W_6(g)]/W_0(g) \quad \text{[Equation 3]}$$

in Equation 2, $W_0$ (g) is an initial weight (g) of the superabsorbent polymer, $W_6$ (g) is the sum of the weight of the superabsorbent polymer and the weight of the apparatus capable of providing a load for the superabsorbent polymer, and $W_7$ (g) is the sum of the weight of the superabsorbent polymer after allowing the superabsorbent polymer to absorb the physiological saline solution under a load (0.3 psi) for 1 hour, and the weight of the apparatus capable of providing the load for the superabsorbent polymer.

The measurement results are shown in the following Table 1.

TABLE 1

| Unit | Temperature of mixture ° C. | Concentration of UV initiator ppmw | SDS ppmw | SBC ppmw | Maximum foaming point sec | Base polymer CRC g/g | Base polymer Vortex sec | Superabsorbent polymer CRC g/g | Superabsorbent polymer Vortex sec | 1 min-absorbency (0.9% NaCl) g/g | 1 min-absorbency (distilled water) g/g | 0.3 AUP g/g |
|---|---|---|---|---|---|---|---|---|---|---|---|---|
| Ex. 1 | 40 | 100 | 100 | 1000 | 60 | 40 | 45 | 34 | 40 | 32 | 125 | 30 |
| Ex. 2 | 40 | 100 | 500 | 1000 | 55 | 38 | 33 | 34 | 30 | 37 | 135 | 29 |
| Ex. 3 | 40 | 100 | 1000 | 1000 | 54 | 36 | 30 | 33 | 25 | 40 | 140 | 28 |
| Ex. 4 | 40 | 150 | 1000 | 1000 | 45 | 34 | 26 | 31 | 21 | 45 | 165 | 28 |
| Ex. 5 | 60 | 100 | 100 | 1000 | 40 | 38 | 40 | 34 | 35 | 34 | 138 | 30 |
| Comparative Ex. 1 | 20 | 100 | 100 | 1000 | 105 | 43 | 65 | 36 | 58 | 25 | 95 | 31 |

TABLE 1-continued

| | | Concentration of UV | | | Maximum foaming | Base polymer | | Superabsorbent polymer | | 1 min-absorbency (0.9% | 1 min-absorbency (distilled | 0.3 |
|---|---|---|---|---|---|---|---|---|---|---|---|---|
| Unit | Temperature of mixture °C. | initiator ppmw | SDS ppmw | SBC ppmw | point sec | CRC g/g | Vortex sec | CRC g/g | Vortex sec | NaCl) g/g | water) g/g | AUP g/g |
| Comparative Ex. 2 | 20 | 30 | 100 | 1000 | 158 | 42 | 70 | 36 | 62 | 23 | 92 | 31 |

As shown in Table 1, it was confirmed that the time taken to reach the maximum foaming point is associated with the absorption rate (vortex) and 1 min-absorbency of the superabsorbent polymer. Specifically, in the case of Examples of the present invention, the time taken to reach the maximum foaming point was short, as compared with that of Comparative Examples, and therefore, their absorption rate and 1 min-absorbency were remarkably improved, as compared with those of Comparative Examples.

The invention claimed is:

1. A method of preparing a superabsorbent polymer, comprising:
    introducing a polymerization initiator and a foaming agent into a reaction mixture while controlling the temperature of the reaction mixture at about 40° C. to about 60° C., wherein the reaction mixture comprising an acrylic acid having at least partially neutralized acid groups, an internal crosslinking agent, and a surfactant;
    polymerizing the reaction mixture to form a hydrogel polymer containing a first cross-linked polymer, wherein a maximum foaming point is reached within 40 to 60 seconds from a polymerization initiation point of the acrylic acid;
    drying, pulverizing, and size-sorting the hydrogel polymer to form a base polymer powder; and
    surface-crosslinking the base polymer powder by heat treatment in the presence of a surface crosslinking solution to form superabsorbent polymer particles,
    wherein the superabsorbent polymer particles have 1 min-absorbency of 125 g/g to 165 g/g for distilled water,
    wherein the superabsorbent polymer particles have 1 min-absorbency of 30 g/g to 45 g/g for a 0.9 wt % sodium chloride aqueous solution,
    wherein the surfactant is sodium dodecyl sulfate and present in the reaction mixture in an amount of 0.01 to 0.1 parts by weight based on 100 parts of the acrylic acid, and
    wherein the foaming agent is sodium bicarbonate and present in an amount of 0.01 to 0.1 parts by weight based on 100 parts of the acrylic acid.

2. The method of claim 1, wherein the polymerization initiator is a thermal polymerization initiator, a photopolymerization initiator, or an oxidation-reduction initiator.

3. The method of claim 1, wherein the base polymer powder is pulverized and size-sorted so that a content of the particles having a particle size of 150 μm to 850 μm is 90% or more.

4. The method of claim 1, wherein the surface crosslinking solution comprises one or more surface crosslinking agents selected from the group consisting of ethylene glycol diglycidyl ether, polyethylene glycol diglycidyl ether, glycerol polyglycidyl ether, propylene glycol diglycidyl ether, polypropylene glycol diglycidyl ether, ethylene glycol, diethylene glycol, propylene glycol, triethylene glycol, tetraethylene glycol, propanediol, dipropylene glycol, polypropylene glycol, glycerin, polyglycerin, butanediol, heptanediol, hexanediol, trimethylol propane, pentaerythritol, sorbitol, calcium hydroxide, magnesium hydroxide, aluminum hydroxide, iron hydroxide, calcium chloride, magnesium chloride, aluminum chloride, and iron chloride.

5. The method of claim 1, wherein the superabsorbent polymer has an absorption rate of 45 seconds or less, as measured according to a vortex measurement method.

6. The method of claim 1, wherein the surface crosslinking solution includes silica and ethylene glycol diglycidyl.

7. The method of claim 6, wherein the internal surface crosslinking agent is polyethylene glycol diacrylate.

* * * * *